United States Patent
Lee et al.

(10) Patent No.: US 8,993,694 B2
(45) Date of Patent: Mar. 31, 2015

(54) ADVANCED TRANSITION METAL CATALYTIC SYSTEMS IN TERMS OF COMONOMER INCORPORATIONS AND METHODS FOR PREPARING ETHYLENE HOMOPOLYMERS OR COPOLYMERS OF ETHYLENE AND ALPHA-OLEFINS USING THE SAME

(71) Applicant: SK Innovation Co., Ltd., Seoul (KR)

(72) Inventors: Hoseong Lee, Seoul (KR); Jongsok Hahn, Daejeon (KR); Dongcheol Shin, Daejeon (KR); Hyosun Lee, Daegu (KR); Chunji Wu, Daegu (KR)

(73) Assignee: SK Innovation Co., Ltd. (KR)

( * ) Notice: Subject to any disclaimer, the term of this patent is extended or adjusted under 35 U.S.C. 154(b) by 30 days.

(21) Appl. No.: 13/870,191

(22) Filed: Apr. 25, 2013

(65) Prior Publication Data
US 2013/0237674 A1  Sep. 12, 2013

Related U.S. Application Data

(62) Division of application No. 13/167,997, filed on Jun. 24, 2011, now abandoned.

(51) Int. Cl.
| C08F 4/642 | (2006.01) |
|---|---|
| C08F 4/6592 | (2006.01) |
| C08F 10/02 | (2006.01) |
| C08F 210/02 | (2006.01) |
| C08F 210/16 | (2006.01) |
| C07F 17/00 | (2006.01) |
| C07F 7/28 | (2006.01) |
| C08F 4/659 | (2006.01) |

(52) U.S. Cl.
CPC ............. *C08F 4/6592* (2013.01); *C07F 17/00* (2013.01); *C07F 7/28* (2013.01); *C08F 4/65908* (2013.01); *C08F 4/65912* (2013.01); *Y10S 526/943* (2013.01)
USPC ........... 526/161; 526/160; 526/165; 526/348; 526/348.2; 526/943

(58) Field of Classification Search
CPC .. C08F 4/65912; C08F 4/6592; C08F 110/02; C08F 210/02; C08F 210/16
USPC ............... 526/160, 161, 165, 348, 943, 348.2
See application file for complete search history.

(56) References Cited

U.S. PATENT DOCUMENTS

| 5,026,798 A | 6/1991 | Canich |
|---|---|---|
| 5,084,534 A | 1/1992 | Welborn, Jr. et al. |
| 5,103,030 A | 4/1992 | Rohrmann et al. |
| 5,703,187 A | 12/1997 | Timmers |
| 2003/0191334 A1* | 10/2003 | Schottek et al. ........... 556/13 |

FOREIGN PATENT DOCUMENTS

| EP | 0416815 | 3/1991 |
|---|---|---|
| EP | 0420436 | 4/1991 |
| EP | 320762 | 4/1992 |
| JP | 02084405 | 3/1990 |
| JP | 03002347 | 1/1991 |
| JP | 63092621 | 4/1998 |
| WO | 03091309 | 11/2003 |

\* cited by examiner

*Primary Examiner* — Caixia Lu
(74) *Attorney, Agent, or Firm* — Cantor Colburn LLP

(57) ABSTRACT

Provided is a homogeneous catalytic system for use in preparing an ethylene homopolymer or a copolymer of ethylene and α-olefin, and more particularly a Group 4 transition metal compound in which a cyclopentadienyl derivative 3,4-positions of which are substituted with alkyls and an electron-donating substituent are crosslinked around a Group 4 transition metal. Also provided is a method of preparing an ethylene homopolymer or a copolymer of ethylene and α-olefin, having high molecular weight, under high-temperature solution polymerization conditions using the catalytic system including such a transition metal compound and a co-catalyst composed of an aluminum compound, a boron compound or a mixture thereof. The catalyst according to present invention has high thermal stability and enables the incorporation of α-olefin, and is thus effective in preparing an ethylene homopolymer or a copolymer of ethylene and α-olefin, having various properties, in industrial polymerization processes.

4 Claims, No Drawings

ADVANCED TRANSITION METAL CATALYTIC SYSTEMS IN TERMS OF COMONOMER INCORPORATIONS AND METHODS FOR PREPARING ETHYLENE HOMOPOLYMERS OR COPOLYMERS OF ETHYLENE AND ALPHA-OLEFINS USING THE SAME

TECHNICAL FIELD

The present invention relates to a homogeneous catalytic system for use in preparing an ethylene homopolymer or a copolymer of ethylene and α-olefin, and more particularly to a Group 4 transition metal catalyst in which a cyclopentadienyl derivative 3,4-positions of which are substituted with alkyls and an electron-donating substituent are crosslinked around the Group 4 transition metal. In addition, the present invention relates to a catalytic system comprising such a transition metal catalyst and a co-catalyst including one or more selected from among aluminoxane and a boron compound and to a method of preparing an ethylene homopolymer or a copolymer of ethylene and α-olefin using the same.

BACKGROUND ART

Conventional ethylene homopolymers or copolymers with α-olefin have been typically prepared using so-called a Ziegler-Natta catalytic system comprising a titanium or vanadium compound as a main catalyst and an alkylaluminum compound as a co-catalyst. Although the Ziegler-Natta catalytic system is highly active for ethylene polymerization, it has non-uniform active sites, so that the produced polymer has a wide molecular weight distribution, and, in particular, the composition distribution is not uniform in copolymerization of ethylene and α-olefin.

Recently, there has been developed a metallocene catalytic system composed of a metallocene compound of Group 4 transition metal of the periodic table, such as titanium, zirconium, hafnium, etc., and a co-catalyst such as methylaluminoxane. Because the metallocene catalytic system is a homogeneous catalyst having single active sites, it enables the preparation of polyethylene having a narrower molecular weight distribution and a more uniform composition distribution, compared to when using the conventional Ziegler-Natta catalytic system. For example, EP Patent Application Publication Nos. 320,762 and 3,726,325, Japanese Patent Laid-open Publication No. Sho. 63-092621, and Japanese Patent Laid-open Publication Nos. Hei. 02-84405 and 03-2347 disclose a metallocene compound such as Cp2TiCl$_2$, Cp$_2$ZrCl$_2$, Cp$_2$ZrMeCl, Cp$_2$ZrMe$_2$, ethylene(IndH$_4$)$_2$ZrCl$_2$, etc., which is activated with a methylaluminoxane co-catalyst, so that ethylene is highly actively polymerized, thereby preparing polyethylene having a molecular weight distribution (Mw/Mn) of 1.5~2.0. However, this catalytic system makes it difficult to obtain a high-molecular-weight polymer. In particular, when this is applied to solution polymerization at a high temperature of at least 140° C., polymerization activity is drastically decreased and (β-dehydrogenation is predominantly carried out, and thus such a catalytic system is known to be unsuitable to prepare a high-molecular-weight polymer having a weight average molecular weight (Mw) of 100,000 or more.

U.S. Pat. No. 5,084,534 by Exxon discloses the preparation of a copolymer having a narrow molecular weight distribution of 1.8~3.0 and a uniform composition distribution by polymerizing ethylene alone or ethylene with 1-hexene or 1-octene at 150~200° C. using a (n-BuCp)$_2$ZrCl$_2$ catalyst and a methylaluminoxane co-catalyst. In addition, EP Patent Nos. 0416815 and 0420436, by Dow, disclose a catalyst the structure of which is geometrically controlled by connecting an amide group in the form of a ring to a cyclopentadiene ligand, and which exhibits high catalytic activity upon polymerizing ethylene alone or ethylene with α-olefin under slurry polymerization or solution polymerization conditions and also increases high reactivity with comonomers, thereby enabling the preparation of a high-molecular-weight polymer having a uniform composition distribution. As in the metallocene catalyst, however, the above catalyst is drastically deteriorated in terms of catalytic stability and comonomer incorporations in proportion to an increase in the temperature under high-temperature solution polymerization conditions of at least 140° C., and economic benefits negate attributed to high material cost, making it difficult to industrially use it.

SUMMARY OF THE INVENTION

Culminating in the present invention, intensive and thorough research was carried out by the present inventors aiming to solve the problems encountered in the related art, which resulted in the finding that a geometrically constrained catalyst in which a cyclopentadienyl derivative 3,4-positions of which are substituted with alkyls and an electron-donating substituent are crosslinked around a Group 4 transition metal is remarkably advanced in terms of comonomer incorporations, making it suitable to prepare an ethylene homopolymer or an elastic copolymer of ethylene and α-olefin, having high molecular weight and high activity using solution polymerization at a high temperature of at least 140° C.

Therefore, an object of the present invention is to provide a catalyst having single active sites, which may exhibit superior thermal stability and is advanced in terms of comonomer incorporations, and a high-temperature solution polymerization method which enables an ethylene homopolymer or a copolymer of ethylene and α-olefin, having various properties, to be easily prepared from an industrial point of view using such a catalyst.

In one aspect to accomplish the above object, the present invention provides a transition metal compound represented by Chemical Formula 1 below, in which a cyclopentadiene derivative 3,4-positions of which are substituted with alkyls an electron-donating substituent are crosslinked around a Group 4 transition metal of the periodic table as a central metal. In addition, the present invention provides a catalyst composition comprising the above transition metal compound and a co-catalyst selected from among an aluminum compound, a boron compound and mixtures thereof, and a method of preparing an ethylene homopolymer or a copolymer of ethylene with α-olefin using the same.

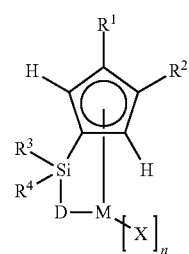

[Chemical Formula 1]

In Chemical Formula 1, M is a Group 4 transition metal of the periodic table;

$R^1$ and $R^2$ are a (C1-C7) alkyl group;

D is —O—, —S—, —N($R^5$)— or —P($R^6$)—, in which $R^5$ and $R^6$ are independently a hydrogen atom, a (C1-C20)alkyl group, a (C3-C20)cycloalkyl group, a (C6-C30)aryl group, a (C6-C30)aryl(C1-C20)alkyl group, a (C1-C20)alkylcarbonyl group, or a (C3-C20)cycloalkylcarbonyl group;

$R^3$ and $R^4$ are independently a hydrogen atom, a (C1-C20) alkyl group, a (C6-C30)aryl group, a (C6-C30)aryl(C1-C20) alkyl group, a (C1-C20)alkoxy group, or a (C1-C20)alkyl or (C3-C20)cycloalkyl substituted siloxy group;

X is independently a halogen atom, a (C1-C20)alkyl group, a (C6-C30)aryl group, a (C6-C30)aryl(C1-C20)alkyl group, a (C1-C20)alkoxy group, a (C1-C20)alkyl or (C3-C20)cycloalkyl substituted siloxy group, a (C1-C20)alkyl, (C6-C30)aryl, (C6-C30)aryl(C1-C20)alkyl or tri(C1-C20)alkylsilyl substituted amino group, a (C1-C20)alkyl, (C6-C30)aryl, (C6-C30)aryl(C1-C20)alkyl or tri(C1-C20)alkylsilyl substituted amide group, a (C1-C20)alkyl, (C6-C30)aryl, (C6-C30) aryl(C1-C20)alkyl or tri(C1-C20)alkylsilyl substituted phosphine group, or a (C1-C20)alkyl, (C6-C30)aryl, (C6-C30) aryl(C1-C20)alkyl or tri(C1-C20)alkylsilyl substituted phosphido group, in which the case where X is a cyclopentadienyl derivative is excluded;

the alkyl group of $R^1$ and $R^2$, the alkyl group, aryl group, arylalkyl group and alkoxy group of $R^3$ and $R^4$, the alkyl group, cycloalkyl group, aryl group, arylalkyl group, alkylcarbonyl group and cycloalkylcarbonyl group of $R^5$ and $R^6$, the alkyl group, aryl group, arylalkyl group and alkoxy group of X may be further substituted with one or more selected from among a (C1-C20)alkyl group, a (C3-C20)cycloalkyl group, a (C6-C30)aryl group, and a (C6-C30)aryl(C1-C20) alkyl group; and n is an integer of 1~4.

In another aspect, the present invention provides a transition metal catalyst composition for preparing an ethylene homopolymer or a copolymer of ethylene and α-olefin, comprising the above transition metal compound and a co-catalyst selected from among an aluminum compound, a boron compound and mixtures thereof, and an ethylene homopolymer or a copolymer of ethylene and α-olefin using the transition metal compound or the catalyst composition.

Below, the present invention is described in more detail. Specifically, M is preferably titanium, zirconium or hafnium. Also, $R^1$ and $R^2$ which are independently located at 3,4-positions of cyclopentadienyl able to form $\eta^5$-bond with M are a (C1-C7)alkyl group, for example, a methyl group, an ethyl group, a n-propyl group, an isopropyl group, a n-butyl group, a sec-butyl group, a tert-butyl group, or a n-pentyl group, and particularly useful is a methyl group.

Also, $R^5$ and $R^6$ are independently a hydrogen atom, a (C1-C20)alkyl group, a (C3-C20)cycloalkyl group, a (C6-C30)aryl group, a (C6-C30)aryl(C1-C20)alkyl group, a (C1-C20)alkylcarbonyl group or a (C3-C20)cycloalkylcarbonyl group, and more specifically a methyl group, an ethyl group, a n-propyl group, an isopropyl group, a sec-butyl group, a tert-butyl group, a cyclohexyl group, a dicyclohexylmethyl group, an adamantyl group, a phenyl group, a phenylmethyl group, a methylcarbonyl group, an ethylcarbonyl group, a n-propylcarbonyl group, an isopropylcarbonyl group, a tert-butylcarbonyl group or an adamantylcarbonyl group. Particularly useful is a tert-butyl group.

Also, $R^3$ and $R^4$ bound with Si are independently a hydrogen atom, a (C1-C20)alkyl group, a (C6-C30)aryl group, a (C6-C30)aryl(C1-C20)alkyl group, a (C1-C20)alkoxy group, or a (C1-C20)alkyl or (C3-C20)cycloalkyl substituted siloxy group, and examples of the (C1-C20)alkyl group include a methyl group, an ethyl group, a n-propyl group, an isopropyl group, a n-butyl group, a sec-butyl group, a tert-butyl group, a n-pentyl group, a neopentyl group, an amyl group, a n-hexyl group, a n-octyl group, a n-decyl group, a n-dodecyl group, a n-pentadecyl group or a n-eicosyl group, and particularly useful is a methyl group, an ethyl group, an isopropyl group, a tert-butyl group or an amyl group; examples of the (C6-C30)aryl group or the (C6-C30)aryl(C1-C20)alkyl group include a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl) methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-dodecylphenyl) methyl group, a (n-tetradecylphenyl)methyl group, a naphthylmethyl group or an anthracenylmethyl group, and particularly useful is benzyl; examples of the (C1-C20)alkoxy group include a methoxy group, an ethoxy group, a n-propoxy group, an isopropoxy group, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group, or a n-eicosoxy group, and particularly useful is a methoxy group, an ethoxy group, an isopropoxy group or a tert-butoxy group; and examples of the (C1-C20)alkyl or (C3-C20)cycloalkyl substituted siloxy group include a trimethylsiloxy group, a triethylsiloxy group, a tri-n-propylsiloxy group, a triisopropylsiloxy group, a tri-n-butylsiloxy group, a tri-sec-butylsiloxy group, a tri-tert-butylsiloxy group, a tri-isobutylsiloxy group, a tert-butyldimethylsiloxy group, a tri-n-pentylsiloxy group, a tri-n-hexylsiloxy group or a tricyclohexylsiloxy group, and particularly useful is a trimethylsiloxy group or a tert-butyldimethylsiloxy group.

X is independently a halogen atom, a (C1-C20)alkyl group, a (C6-C30)aryl group, a (C6-C30)aryl(C1-C20)alkyl group, a (C1-C20)alkoxy group, a (C1-C20)alkyl or (C3-C20)cycloalkyl substituted siloxy group, a (C1-C20)alkyl, (C6-C30) aryl, (C6-C30)aryl(C1-C20)alkyl or tri(C1-C20)alkylsilyl substituted amino group, a (C1-C20)alkyl, (C6-C30)aryl, (C6-C30)aryl(C1-C20)alkyl or tri(C1-C20)alkylsilyl substituted amide group, a (C1-C20)alkyl, (C6-C30)aryl, (C6-C30) aryl(C1-C20)alkyl or tri(C1-C20)alkylsilyl substituted phosphine group, or a (C1-C20)alkyl, (C6-C30)aryl, (C6-C30) aryl(C1-C20)alkyl or tri (C1-C20)alkylsilyl substituted phosphido group, wherein the case where X is a cyclopentadienyl derivative is excluded. Examples of the halogen atom include fluorine, chlorine, bromine or iodine; examples of the (C1-C20)alkyl group include a methyl group, an ethyl group, a n-propyl group, an isopropyl group, a n-butyl group, a sec-butyl group, a tert-butyl group, a n-pentyl group, a neopentyl group, an amyl group, a n-hexyl group, a n-octyl group, a n-decyl group, a n-dodecyl group, a n-pentadecyl group or a n-eicosyl group, and particularly useful is a methyl group, an ethyl group, an isopropyl group, a tert-butyl group or an amyl group; examples of the (C6-C30)aryl(C1-C20)

alkyl group include a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl) methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl) methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl) methyl group, an (ethylphenyl)methyl group, a (n-propylphenyl)methyl group, an (isopropylphenyl)methyl group, a (n-butylphenyl)methyl group, a (sec-butylphenyl) methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-decylphenyl)methyl group, a (n-tetradecylphenyl)methyl group, a naphthylmethyl group or an anthracenylmethyl group, and particularly useful is a benzyl group; examples of the (C1-C20)alkoxy group include a methoxy group, an ethoxy group, a n-propoxy group, an isopropoxy group, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group, or a n-eicosoxy group, and particularly useful is a methoxy group, an ethoxy group, an isopropoxy group or a tert-butoxy group; examples of the (C1-C20)alkyl or (C3-C20)cycloalkyl substituted siloxy group include a trimethylsiloxy group, a triethylsiloxy group, a tri-n-propylsiloxy group, a triisopropylsiloxy group, a tri-n-butylsiloxy group, a tri-sec-butylsiloxy group, a tri-tert-butylsiloxy group, a tri-isobutylsiloxy group, a tert-butyldimethylsiloxy group, a tri-n-pentylsiloxy group, a tri-n-hexylsiloxy group or a tricyclohexylsiloxy group, and particularly useful is a trimethylsiloxy group or a tert-butyldimethylsiloxy group; examples of the (C1-C20)alkyl, (C6-C30)aryl, (C6-C30)aryl(C1-C20)alkyl or (C1-C20) alkylsilyl substituted amino group include a dimethylamino group, a diethylamino group, a di-n-propylamino group, a diisopropylamino group, a di-n-butylamino group, a di-sec-butylamino group, a di-tert-butylamino group, a diisobutylamino group, a tert-butylisopropylamino group, a di-n-hexylamino group, a di-n-octylamino group, a di-n-decylamino group, a diphenylamino group, a dibenzylamino group, a methylethylamino group, a methylphenylamino group, a benzylhexylamino group, a bistrimethylsilylamino group or a bi-tert-butyldimethylsilylamino group, and particularly useful is a dimethylamino group or a diethylamino group; examples of the (C1-C20)alkyl, (C6-C30)aryl, (C6-C30)aryl (C1-C20)alkyl or (C1-C20)alkylsilyl substituted amide group include a dibenzylamide group, a methylethylamide group, a methylphenylamide group or a benzylhexylamide group, and particularly useful is a diphenylamide group; examples of the (C1-C20)alkyl, (C6-C30)aryl, (C6-C30)aryl (C1-C20)alkyl or (C1-C20)alkylsilyl substituted phosphine group include a dimethylphosphine group, a diethylphosphine group, a di-n-propylphosphine group, a diisopropylphosphine group, a di-n-butylphosphine group, a di-sec-butylphosphine group, a di-tert-butylphosphine group, a diisobutylphosphine group, a tert-butylisopropylphosphine group, a di-n-hexylphosphine group, a di-n-octylphosphine group, a di-n-decylphosphine group, a diphenylphosphine group, a dibenzylphosphine group, a methylethylphosphine group, a methylphenylphosphine group, a benzylhexylphosphine group, a bistrimethylsilylphosphine group or a bis-tert-butyldimethylsilylphosphine group; and examples of the (C1-C20)alkyl, (C6-C30)aryl, (C6-C30)aryl(C1-C20)alkyl or (C1-C20)alkylsilyl substituted phosphido group include a dibenzylphosphido group, a methylethylphosphido group, a methylphenylphosphido group, a benzylhexylphosphido group or a bistrimethylsilylphosphido group.

Also, n is an integer of 1~4 selected by the oxidation number of transition metal, and preferably an integer of 1 or 2.

The present invention provides an ethylene homopolymer or a copolymer of ethylene and α-olefin, prepared using the transition metal compound as a catalyst.

On the other hand, in order to use the transition metal compound of Chemical Formula 1 as a catalyst component active for olefin polymerization, while the ligand X of the transition metal compound according to the present invention is extracted and the central metal thereof is cationized, a boron compound, an aluminum compound or a mixture thereof, corresponding to a counter ion having weak bondability, namely, an anion, is utilized as a co-catalyst. As such, the aluminum compound which is responsible for removing a small amount of polar material such as water acting as catalytic poison may function as an alkylating agent in the case where the ligand X is halogen.

Useful as the co-catalyst in the present invention, the boron compound may be selected from among compounds of Chemical Formulas 2, 3 and 4 below as disclosed in U.S. Pat. No. 5,198,401.

$B(R^7)_3$                                    [Chemical Formula 2]

$[R^8]^+[B(R^7)_4]^-$                        [Chemical Formula 3]

$[(R^9)_qZH]^+[B(R^7)_4]^-$                [Chemical Formula 4]

[In Chemical Formulas 2 to 4, B is a boron atom; $R^7$ is a phenyl group, in which the phenyl group may be further substituted with three to five substituents selected from among a fluorine atom, a fluorine-substituted or unsubstituted (C1-C20)alkyl group, and a fluorine-substituted or unsubstituted (C1-C20)alkoxy group; $R^8$ is a (C5-C7)cycloalkyl radical, a (C1-C20)alkyl(C6-C20)aryl radical or a (C6-C30)aryl (C1-C20)alkyl radical, for example, a triphenylmethyl radical; Z is a nitrogen atom or a phosphorus atom; $R^9$ is a (C1-C20)alkyl radical or an anilinium radical substituted with two (C1-C4)alkyl groups along with a nitrogen atom; and q is an integer of 2 or 3.]

Preferred examples of the boron-based co-catalyst include one or more selected from among tris(pentafluorophenyl) borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,2,4-trifluorophenyl)borate, phenylbis(pentafluorophenyl)borate and tetrakis(3,5-bistrifluoromethylphenyl) borate, and specific combination examples thereof include ferrocenium tetrakis(pentafluorophenyl)borate, 1,1'-dimethylferrocenium tetrakis(pentafluorophenyl)borate, tetrakis (pentafluorophenyl)borate, triphenylmethyl tetrakis(pentafluorophenyl)borate, triphenylmethyl tetrakis(3,5-bistrifluoromethylphenyl)borate, triethylammonium tetrakis (pentafluorophenyl)borate, tripropylammonium tetrakis (pentafluorophenyl)borate, tri(n-butyl)ammonium tetrakis (pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate or tri(dimethylphenyl)phosphonium tetrakis(pentafluorophenyl)borate, and particularly useful is N,N-dimethylanilinium tetrakis(pentafluorophenyl)borate, triphenylmethyl tetrakis(pentafluorophenyl)borate or tris(pentafluoro)borane.

The aluminum compound used in the present invention may include an aluminoxane compound of Chemical Formula 5 or 6 below, an organic aluminum compound of Chemical Formula 7 below, or an organic aluminum hydrocarbyl oxide compound of Chemical Formula 8 or 9 below.

$$(-Al(R^{10})-O-)_m \quad \text{[Chemical Formula 5]}$$

$$(R^{10})_2Al-(-O(R^{10})_p-(R^{10})_2 \quad \text{[Chemical Formula 6]}$$

$$(R^{11})_2Al(E)_{3-r} \quad \text{[Chemical Formula 7]}$$

$$(R^{12})_2AlOR^{13} \quad \text{[Chemical Formula 8]}$$

$$R^{12}Al(OR^{13})_2 \quad \text{[Chemical Formula 9]}$$

[In Chemical Formulas 5 to 9, $R^{10}$ is a linear or non-linear (C1-C20)alkyl group, and preferably is a methyl group or an isobutyl group; m and p are independently an integer of 5~20; $R^{11}$ and $R^{12}$ are independently a (C1-C20)alkyl group; E is a hydrogen atom or a halogen atom; r is an integer of 1~3; and $R^{13}$ is a (C1-C20)alkyl group or a (C6-C30)aryl group.]

Useful as the co-catalyst, the aluminum compound is one or more selected from aluminoxane and organic aluminum, and the aluminoxane compound may include methylaluminoxane, modified methylaluminoxane or tetraisobutylaluminoxane; and the organic aluminum compound is selected from among trialkylaluminum, dialkylaluminum chloride, alkylaluminum dichloride, and dialkylaluminum hydride. Specific examples of the organic aluminum compound include trialkylaluminum, including trimethylaluminum, triethylaluminum, tripropylaluminum, triisobutylaluminum and trihexylaluminum; dialkylaluminum chloride, including dimethylaluminum chloride, diethylaluminum chloride, dipropylaluminum chloride, diisobutylaluminum chloride, and dihexylaluminum chloride; alkylaluminum dichloride, including methylaluminum dichloride, ethylaluminum dichloride, propylaluminum dichloride, isobutylaluminum dichloride and hexylaluminum dichloride; and dialkylaluminum hydride, including dimethylaluminum hydride, diethylaluminum hydride, dipropylaluminum hydride, diisobutylaluminum hydride and dihexylaluminum hydride, and preferably useful is trialkylaluminum, and more preferably is triethylaluminum or triisobutylaluminum, in which the molar ratio of central transition metal (M) to aluminum atom (Al) is 1:50~5,000.

As the ratio of transition metal compound to co-catalyst, the molar ratio of central transition metal (M) to boron atom (B) to aluminum atom (Al) is 1:0.1~100:10~1,000, and more preferably 1:0.5~5:25~500. The preparation of an ethylene homopolymer or a copolymer of ethylene and α-olefin is possible within the above range, and the range of the ratio may vary depending on the purity of reaction.

In another aspect, the present invention provides an ethylene homopolymer or a copolymer of ethylene and α-olefin, prepared using the transition metal compound as the catalyst composition, and the preparation method is performed in a solution phase by brining the transition metal compound, the co-catalyst, and ethylene or α-olefin comonomer into contact with each other in the presence of an appropriate solvent. As such, the transition metal compound and the co-catalyst component may be separately added into a reactor or respective components may be pre-mixed and then introduced into a reactor.

The organic solvent used in the preparation method is preferably a (C3-C20)hydrocarbon, and specific examples thereof include butane, isobutane, pentane, hexane, heptane, octane, isooctane, nonane, decane, dodecane, cyclohexane, methylcyclohexane, benzene, toluene and xylene.

Specifically, upon preparation of the ethylene homopolymer, an ethylene monomer is used alone, and the pressure of ethylene suitable for the present invention is 1~1000 atm, and preferably 10~150 atm. When the pressure falls in the above range, a reactor made of a thin material may be used and there is no need for an additional compression process, thus generating economic benefits and increasing the yield of polymer. The polymerization temperature is 60~300° C., and preferably 80~250° C. If the polymerization temperature is 80° C. or higher, low-density polymers may be prepared thanks to advanced comonomer incorporations. In contrast, if the polymerization temperature is 250° C. or lower, the conversion from ethylene into polymer may increase, thus obtaining high-density polymers.

Also in the method of preparing an ethylene homopolymer or a copolymer of ethylene and α-olefin using the transition metal catalyst composition, the comonomer which is polymerized with ethylene may include α-olefin of (C3-C18) hydrocarbon, and is preferably selected from among propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-octadecene, and 1-itocene. More preferably, 1-butene, 1-hexene, 1-octene, or 1-decene may be copolymerized with ethylene. In this case, the preferred ethylene pressure and polymerization temperature are the same as in the preparation of high-density polyethylene, and the ethylene copolymer prepared using the method according to the present invention has an ethylene content of 50 wt % or more, preferably 60 wt % or more, and more preferably 60~99 wt %. As mentioned above, when using α-olefin of (C4-C10) hydrocarbon as the comonomer, the resultant linear low-density polyethylene (LLDPE) has a density of 0.850~0.950 g/cc, and preferably the preparation of an olefinic copolymer having a density of 0.860~0.940 g/cc is possible.

In order to regulate the molecular weight upon preparation of the ethylene homopolymer or copolymer according to the present invention, hydrogen may be used as a molecular weight regulating agent, so that a weight average molecular weight (Mw) is 80,000~500,000, and a molecular weight distribution (Mw/Mn) which is the ratio of weight average molecular weight/number average molecular weight is 1.5~4.1.

The catalyst composition according to the present invention is present in a uniform form in the polymerization reactor, and thus is preferably applied to solution polymerization that is carried out at a temperature not lower than the melting point of the corresponding polymer. However, as disclosed in U.S. Pat. No. 4,752,597, a heterogeneous catalytic system resulting from supporting the above transition metal compound and a co-catalyst on a porous metal oxide support may be employed in slurry polymerization or gas polymerization.

According to the present invention, a transition metal compound or a catalyst composition including the transition metal compound can be easily produced at high yield using a simple process by reducing the number of alkyls except for a specific portion of cyclopentadiene, thus generating economic benefits. Furthermore, the catalyst has high thermal stability and thus maintains high catalytic activity upon olefin polymerization under high-temperature solution polymerization conditions and also enables the preparation of a high-molecular-weight polymer at high yield. Also, because the catalyst is advanced in terms of comonomer incorporations, its industrial availability is higher compared to conventionally known metallocene and non-metallocene based catalysts having single active sites.

Thus, the transition metal catalyst composition and the preparation method according to the present invention can be efficiently utilized for preparing copolymers of ethylene and α-olefin, having various properties and elastic moduli.

DETAILED DESCRIPTION OF THE INVENTION

A better understanding of the present invention may be obtained via the following examples that are set forth to illustrate, but are not to be construed as limiting, the present invention.

Unless otherwise stated, all ligands and catalyst synthesis tests were performed using standard Schlenk or glove box techniques in a nitrogen atmosphere, and the organic solvent used in the reaction was refluxed in the presence of sodium metal and benzophenone to remove water, and then distilled just before use. The $^1$H-NMR analysis of the synthesized ligand and catalyst was performed at room temperature using a Bruker 500 MHz spectrometer.

As a polymerization solvent, cyclohexane was sequentially passed through Q-5 catalyst (available from BASF), silica gel, and activated alumina of the reactor, and bubbled with high-purity nitrogen, thus sufficiently removing water, oxygen and other catalyst poisoning materials, and then used.

The resultant polymer was analyzed via the following methods.

1. Melt Flow Index (MI)
Measurement was performed according to ASTM D 2839.
2. Density
According to ASTM D 1505, measurement was performed using a density gradient tube.
3. Analysis of Melting Point (Tm)
Measurement was performed under $2^{nd}$ heating conditions at a rate of 10° C./min in a nitrogen atmosphere using Dupont DSC2910.
4. Molecular weight and Molecular weight distribution
Measurement was performed in the presence of 1,2,3-trichlorobenzene solvent at a rate of 1.0 mL/min at 135° C. using PL210 GPC equipped with PL Mixed-BX2+preCol, and the molecular weight was corrected using a PL polystyrene standard material.
5. α-Olefin Content of Copolymer (wt %)
Measurement was performed in $^{13}$C-NMR mode at 120° C. in the presence of a solvent mixture comprising 1,2,4-trichlorobenzene/$C_6D_6$ (7/3 weight ratio) at 125 MHz using a Bruker DRX500 nuclear magnetic resonance spectrometer. (Reference: Randal, J. C. *JMS-Rev. Macromol. Chem. Phys.* 1980, C29, 201)

Preparative Example 1

Synthesis of (dichloro) (tert-butylamido) (3,4-dimethylcyclopentadienyl) (dimethylsilane)titanium (IV)

(1) Synthesis of Crotonic Acid Isopropyl Ester

Crotonic acid (193.7 g, 2.25 mol) was dissolved in 2-propanol (860 mL, 11.25 mol) in a 2 L flask and then well stirred, after which sulfuric acid (24 mL, 0.45 mol) was slowly added in droplets to the mixture and refluxed and stirred for 48 hours or longer. The stirred mixture was cooled to room temperature, after which the obtained mixture was washed with distilled water (1000 mL), and the organic layer was separated, neutralized and subjected to atmospheric distillation (80° C.), thus obtaining 220 g (1.71 mol, yield 76.3%) of crotonic acid isopropyl ester.

$^1$H-NMR ($C_6D_6$) δ=1.01~1.06 (d, 6H), 1.26~1.37 (q, 3H), 5.01~5.08 (m, 1H), 5.70~5.79 (m, 1H), 6.82~6.93 (m, 1H) ppm (2) Synthesis of 3,4-Dimethyl-2-Cyclopentenone 1 L of polyphosphoric acid was added into a 2 L flask, purged with nitrogen, and then refluxed and stirred at 100° C., after which crotonic acid isopropyl ester (76.9 g, 0.6 mol) was slowly added in droplets thereto, and the mixture was stirred for 3 hours and thus turned into dark brown. The mixture thus obtained was mixed with ice water (500 mL) and then neutralized with sodium carbonate, after which the organic layer was extracted with ethylether and then subjected to vacuum distillation (105° C., 40 torr), thus obtaining 56 g (0.51 mol, yield 84.7%) of 3,4-dimethyl-2-cyclopentenone as a colorless transparent liquid.

$^1$H-NMR (CDCl$_3$) δ=1.05~1.09 (d, 3H), 1.83~1.87 (q, 1H), 1.98 (s, 3H), 2.45~2.51 (q, 1H), 2.67~2.70 (m, 1H), 5.73 (s, 1H) ppm (3) Synthesis of tert-butyl-1-(3,4-dimethylcyclopentadienyl)-1,1-dimethylsilaneamine In a nitrogen atmosphere, lithium aluminum hydride (6.07 g, 0.16 mol) was dissolved in diethylether (250 mL), and 3,4-dimethyl-2-cyclopentenone (33.95 g, 0.31 mol) was slowly added in droplets thereto at 0° C. Refluxing for 30 minutes and cooling to 0° C. via room temperature were performed, after which distilled water (15 mL) was slowly added in droplets thereto and thus unreacted lithium aluminum hydride was removed. The reaction mixture was slowly added to dilute sulfuric acid and the organic layer was extracted with diethylether and then subjected to vacuum distillation, thus obtaining 21.2 g of 2,3-dimethylcyclopentadiene as a yellow liquid. This solution was transferred into a flask and dissolved in pentane (200 mL), after which n-butyl lithium (141 mL, 0.225 mol, 1.6 M) was added in droplets thereto at −78° C. The temperature was increased to room temperature and the reaction was then carried out for 12 hours, thus obtaining 10.5 g (yield 46.9%) of 1,2-dimethyl-cyclopentadienyl lithium as off-white powder. 5.45 g (54.5 mmol) of the powder was placed in a flask containing diethylether (80 mL), and dichlorodimethylsilane (6.8 mL, 54.5 mmol) was then added in droplets thereto at −78° C. Subsequently, the temperature was increased to room temperature and the reaction was carried out for 12 hours or longer. Diethylether was removed using vacuum distillation, and the resultant product was washed with pentane, thus obtaining 6.35 g (yield 62.4%) of dimethylsilyl-3,4-dimethylcyclopentadienyl chloride as a yellow liquid. This liquid was transferred into a flask without purification and then dissolved in tetrahydrofuran (90 mL), after which lithium-tert-butylamine (2.69 g, 34.0 mmol) was slowly added in droplets thereto at −78° C. The reaction was carried out at room temperature for 12 hours or longer and the solvent was then completely removed using vacuum drying, after which the resultant product was extracted with purified pentane, thus obtaining, as a yellow liquid, 6.15 g (27.5 mmol, yield 80.9%) of Cert-butyl-1-(3,4-dimethylcyclopentadienyl)-1,1-dimethylsilaneamine.

$^1$H NMR (C$_6$D$_6$): δ=0.00 (s, 6H), 0.28(s, 3H), 1.05 (s, 3H), 1.07 (s, 9H), 1.09 (s, 3H), 1.85 (s, 2H), 1.94 (s, 2H), 1.98(s, 6H), 2.89 (t, 1H), 3.17 (t, 1H), 6.16 (s, 2H), 6.31~6.70 (m, 1H) ppm

(4) Synthesis of (Dichloro)(Tert-Butylamido)(3,4-Dimethylcyclopentadienyl)(Dimethylsilane)Titanium (IV)

tert-Butyl-1-(3,4-dimethylcyclopentadienyl)-1,1-dimethylsilaneamine (6.15 g, 27.5 mmol) was placed in a flask and dissolved in diethylether (100 mL) in a nitrogen atmosphere, after which n-butyl lithium (22.0 mL) was slowly added in droplets thereto at −78° C. The temperature was gradually increased to room temperature and the reaction was carried out for 12 hours or longer. The solvent was completely removed using vacuum drying and the resultant product was washed with pentane, thus obtaining as off-white powder 5.24 g (yield 81.0%) of lithium (tert-butylamido)(3,4-dimethylcyclopentadienyl)dimethylsilane. 3.00 g (12.8 mmol) of the powder and tetrachlorobis(tetrahydrofuran)titanium (IV) (4.26 g, 12.8 mmol) were placed together in a flask and toluene (50 mL) was added thereto so that the reaction was carried out at 80° C. for 24 hours or longer. The temperature was decreased to room temperature and filtration was conducted thus removing lithium chloride, and solvent was removed using vacuum drying, after which the resultant product was extracted with pentane and recrystallized, thus obtaining as a yellow solid 1.73 g (yield 39.9%) of (dichloro) (tert-butylamido)(3,4-dimethylcyclopentadienyl)(dimethylsilane)titanium (IV).

$^1$H NMR (C$_6$D$_6$): δ=0.26 (s, 6H), 1.40 (s, 9H), 2.04 (s, 6H), 5.91 (s, 2H) ppm; $^{13}$C NMR(C$_6$D$_6$): δ=0.97, 13.41, 33.18, 105.91, 123.05, 127.84, 128.22, 133.45 ppm.

Preparative Example 2

Synthesis of (dichloro) (tert-butylamido) (3,4-dimethylcyclopentadienyl) (dimethylsilane)zirconium (IV)

Lithium(tert-butylamido)3,4-dimethylcyclopentadienyldimethylsilane (0.9 g, 3.83 mmol) and zirconium (IV) chloride (0.891 g, 3.83 mmol) were placed together in a flask and toluene (20 mL) was added thereto so that the reaction was carried out at 80° C. for 24 hours or longer. The temperature was decreased to room temperature and filtration was conducted thus removing lithium chloride and solvent was removed using vacuum drying, after which the resultant product was extracted with pentane and recrystallized, thus obtaining as a pale brown solid 0.89 g (yield 60.5%) of (dichloro)(tert-butylamido)(3,4-dimethylcyclopentadienyl) (dimethylsilane)zirconium (IV).

$^1$H NMR (C$_6$D$_6$): δ=0.30 (s, 6H), 1.31 (s, 9H), 2.00 (s, 6H), 5.90 (s, 2H) ppm; $^{13}$C NMR(C$_6$D$_6$): δ=0.07, 14.36, 32.65, 107.74, 126.86, 126.91, 128.82, 139.34 ppm.

Comparative Preparative Example 1

Synthesis of (dichloro) (tert-butylamido)(2,3,4,5-tetramethylcyclopentadienyl)(dimethylsilane)titanium (IV)

(1) Synthesis of (tert-butylamino)(2,3,4,5-tetramethylcyclopenta-2,4-dienyl)dimethylsilane 2,3,4,5-tetramethylcyclopenta-2,4-diene (3.67 g, 30 mmol) was added into a flask containing tetrahydrofuran (100 mL), n-butyl lithium (12 mL) was added in droplets thereto at 0° C., and the reaction temperature was gradually increased to room temperature so that the reaction was carried out for 8 hours. This solution was cooled to −78° C., dichloromethylsilane (3.87g, 30 mmol) was slowly added in droplets thereto, and then the reaction was carried out for 12 hours. After the reaction, the volatile material was removed, and the resultant product was extracted with hexane (100 mL), after which the volatile material was removed, thereby obtaining as pale yellow oil 5.5 g of (chloro) (dimethyl) (2,3,4,5-tetramethylcyclopentadienyl)silane. The (chloro)(dimethyl)(2,3,4,5-tetramethylcyclopentadienyl)silane thus obtained was dissolved in tetrahydrofuran (100 mL) without additional purification, after which lithium tert-butylamide (2.02 g) was added in droplets thereto at 0° C. and the reaction was carried out at room temperature for 2 hours. After the reaction, the volatile material was removed, and the resultant product was extracted with hexane (100 mL), thus obtaining as pale yellow oil 6.09 g (yield 81%) of (tert-butylamino) (2,3,4,5-tetramethylcyclopenta-2,4-dienyl)dimethylsilane.

$^1$H-NMR (C$_6$D$_6$) δ=0.11 (s, 6H), 1.11 (s, 9H), 1.86 (s, 6H), 2.00 (s, 6H) 2.78 (s, 1H) ppm

(2) Synthesis of (dichloro) (tert-butylamido)(2,3,4,5-tetramethylcyclopentadienyl) (dimethylsilane)titanium (IV)

(tert-Butylamino) (2,3,4,5-tetramethylcyclopenta-2,4-dienyl)dimethylsilane (6.09 g 24.2 mmol) was dissolved in diethylether (100 mL), and n-butyl lithium (9.7 mL) was added in droplets thereto at −78° C., after which the reaction temperature was gradually increased to room temperature and the reaction was carried out for 12 hours. After the reaction, the volatile material was removed, and the resultant product was extracted with hexane (100 mL) thus obtaining 6.25 g of an orange-colored solid. The solid thus obtained was dissolved in toluene (100 mL), and tetrachlorotitanium (IV) (4.50 g 23.7 mmol) was added in droplets thereto at −78° C., after which the reaction temperature was increased to room temperature and the reaction was carried out for 7 hours. After completion of the reaction, the volatile material was removed, and the resultant product was extracted with purified pentane (100 mL) and recrystallized at −35° C., filtered and then vacuum dried, thus obtaining as an orange-colored solid 0.87 g(yield 10%) of (dichloro) (tert-butylamido) (2,3,4,5-tetramethylcyclopentadienyl) (dimethylsilane)titanium (IV).

$^1$H-NMR (C$_6$D$_6$) δ=0.43 (s, 6H), 1.43 (s, 9H), 2.00 (s, 6H), 2.01 (s, 6H) ppm

Comparative Preparative Example 2

Synthesis of (dichloro)(tert-butylamido) (2,3,4,5-tetramethylcyclopentadienyl) (dimethylsilane)zirconium (IV)

1.3 g (yield 13.3%) of (dichloro)(tert-butylamido) (2,3,4,5-tetramethylcyclopentadienyl) (dimethylsilane)zirconium (IV) was synthesized in the same manner as in Comparative Preparative Example 1, with the exception that 5.52 g (23.7 mmol) of tetrachlorozirconium (IV) was used.

$^1$H-NMR (C$_6$D$_6$) δ=0.40 (s, 6H), 1.40 (s, 9H), 1.97 (s, 6H), 2.00 (s, 6H) ppm.

Example 1

Ethylene and 1-octene was copolymerized via the following procedures using a batch type polymerization device.

Specifically, 1170 mL of cyclohexane and 30 mL of 1-octene were added into a 2000 mL stainless steel reactor sufficiently dried and purged with nitrogen, after which 22.1 mL of modified methylaluminoxane-7 (available from Akzo Nobel, modified MAO-7, 7 wt % Al Isopar solution) 54.2 mM toluene solution was fed into the reactor. The temperature of the reactor was increased to 80° C., after which 0.4 mL of the (dichloro) (tert-butylamido) (3,4-dimethylcyclopentadienyl) (dimethylsilane)titanium (IV) (5.0 mM toluene solution) synthesized in Preparative Example 1 and 2.0 mL of triphenylmethylinium tetrakis pentafluorophenylborate (99%, Boulder Scientific) 10 mM toluene solution were sequentially added thereto, and the inner pressure of the reactor was adjusted up to 30 kg/cd with ethylene, after which polymerization was carried out. During the reaction time of 5 minutes, the temperature arrived at 162.2° C. in maximum. After 5 minutes, 100 mL of ethanol containing 10 vol % hydrochloric acid aqueous solution was added thereto, thus terminating the polymerization, after which stirring was performed using 1.5 L of ethanol for 1 hour, followed by filtering and separating the reaction product. The recovered reaction product was dried in a vacuum oven at 60° C. for 8 hours, yielding 62.8g of a polymer. The polymer had a melting point of 117.48° C., a melt index of 0.016, and a density of 0.9124 g/cc, and upon analysis using gel chromatography, a weight average molecular weight (Mw) of 202,000 g/mol, a molecular weight distribution (Mw/Mn) of 4.05, and a 1-octene content of 7.68 wt %.

Example 2

Ethylene and 1-octene were copolymerized in the same manner as in Example 1, with the exception that the reaction temperature was increased up to 140° C. before adding the catalyst. During the reaction time of 5 minutes, the temperature arrived at 180.9° C. in maximum, and 48.04 g of a polymer was finally obtained. The polymer had a melting point of 119.02° C., a melt index of 1.5, a density of 0.9152 g/cc, and upon analysis using gel chromatography, a Mw of 109,100 g/mol, a Mw/Mn of 2.33, and a 1-octene content of 4.98 wt %.

Example 3

Ethylene and 1-octene were copolymerized in the same manner as in Example 1, with the exception that 0.4 mL of the (dichloro) (tert-butylamido) (3,4-dimethylcyclopentadienyl) (dimethylsilane)zirconium (IV) (5.0 mM toluene solution) synthesized in Preparative Example 2 was added and the reaction time was set to 10 minutes. During the reaction time of 10 minutes, the temperature arrived at 98.2° C. in maximum, and 4.62 g of a polymer was finally obtained. The polymer had a melting point of 133.28° C., a melt index of 0.165, a density of 0.9370 g/cc, and upon analysis using gel chromatography, a Mw of 211,600 g/mol, a Mw/Mn of 3.13, and a 1-octene content of 0.82 wt %.

Comparative Example 1

Ethylene and 1-octene were copolymerized in the same manner as in Example 1, with the exception that the (dichloro) (tert-butylamido) (2,3,4,5-tetramethylcyclopentadienyl) (dimethylsilane)titanium (IV) synthesized in Comparative Preparative Example 1 was added. During the reaction time of 5 minutes, the temperature arrived at 163.0° C. in maximum, and 66.68 g of a polymer was finally obtained. The polymer had a melting point of 116.35° C., a melt index of 0.004, a density of 0.9420 g/cc, and upon analysis using gel chromatography, a Mw of 247,800 g/mol, a Mw/Mn of 7.30, and a 1-octene content of 6.55 wt %.

Comparative Example 2

Ethylene and 1-octene were copolymerized in the same manner as in Example 1, with the exception that the reaction temperature was increased up to 140° C. before adding the catalyst, and the (dichloro) (tert-butylamido)(2,3,4,5-tetramethylcyclopentadienyl) (dimethylsilane)titanium (IV) synthesized in Comparative Preparative Example 1 was added. During the reaction time of 5 minutes, the temperature arrived at 184.4° C. in maximum, and 40.03 g of a polymer was finally obtained. The polymer had a melting point of 116.21° C., a melt index of 0.56, a density of 0.9218 g/cc, and upon analysis using gel chromatography, a Mw of 106,000 g/mol, a Mw/Mn of 4.31, and a 1-octene content of 6.34 wt %.

Comparative Example 3

Ethylene and 1-octene were copolymerized in the same manner as in Example 1, with the exception that 0.4 mL of the (dichloro) (tert-butylamido)(2,3,4,5-tetramethylcyclopentadienyl) (dimethylsilane)zirconium (IV) (5.0 mM toluene solution) synthesized in Comparative Preparative Example 2 was added and the reaction time was set to 10 minutes. During the reaction time of 10 minutes, the temperature arrived at 102.1° C. in maximum, and 16.49 g of a polymer was finally obtained. The polymer had a melting point of 125.93° C., a melt index of 0.087, a density of 0.9405 g/cc, and upon analysis using gel chromatography, a Mw of 426,800 g/mol, a Mw/Mn of 3.31, and a 1-octene content of 2.2 wt %.

As is apparent from the above examples, in the polymerization of ethylene alone and in combination with 1-octene under the above polymerization conditions, the polymers could be produced at higher yield, and olefin copolymers having higher 1-octene contents were obtained under the same conditions, compared to the comparative examples. In particular, low-density copolymers could be successfully prepared from ethylene and 1-octene.

Although the preferred embodiments of the present invention have been disclosed for illustrative purposes, those skilled in the art will appreciate that various modifications, additions, and substitutions are possible, without departing from the scope and spirit of the invention as disclosed in the accompanying claims.

What is claimed are:

1. A method of preparing an ethylene homopolymer or a copolymer of ethylene and α-olefin having a weight average molecular weight of 80,000 to 500,000 and a molecular weight distribution (Mw/Mn) of 1.5 to 4.1 using a transition metal catalyst composition represented by Chemical Formula 1 below, wherein a density of the copolymer of ethylene and α-olefin is 0.850 to 0.940 g/cc:

[Chemical Formula 1]

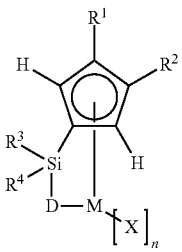

wherein,

M is titanium or zirconium;

R¹ and R² are a (C1-C7) alkyl group which is independently located at 3,4-positions of cyclopentadienyl able to form η⁵-bond with M;

D is —N(R⁵), in which R⁵ is independently a hydrogen atom, or a (C1-C20) alkyl group;

R³ and R⁴ are independently a hydrogen atom or a (C1-C20) alkyl group;

X is independently a halogen atom, or a (C1-C20) alkyl group; and n is an integer of 1 or 2.

2. The method of claim 1, wherein the R5 independently is selected from a methyl group, an ethyl group, a n-propyl group, an isopropyl group, a sec-butyl group or a tert-butyl group, a cyclohexyl group, a dicyclohexylmethyl group, an adamantyl group, a phenyl group, a phenylmethyl group, a methylcarbonyl group, an ethylcarbonyl group, a n-propylcarbonyl group, an isopropylcarbonyl group, a tert-butylcarbonyl group, and an adamantylcarbonyl group.

3. The method of claim 1, wherein a comonomer which is polymerized with ethylene is one or more selected from propylene, 1-butene, 1-pentene, 1-hexene, 1-heptene, 1-octene, 1-decene, 1-undecene, 1-dodecene, 1-tetradecene, 1-hexadecene, and 1-itocene, and the copolymer of ethylene and a-olefin has an ethylene content of 50 wt % or more.

4. The method of claim 3, wherein a pressure of the ethylene in a reactor is 6 to 150 atm, and a polymerization temperature is 60° C. to 250° C.

* * * * *